(12) United States Patent
Bellini et al.

(10) Patent No.: US 8,728,524 B2
(45) Date of Patent: May 20, 2014

(54) BIOMATERIALS CONSISTING OF SULPHATED HYALURONIC ACID AND GELLAN TO BE USED IN THE PREVENTION OF SPINAL ADHESIONS

(75) Inventors: Davide Bellini, Albignasego (IT); Cristina Longinotti, Montegrotto Terme (IT); Vittorio Crescenzi, Rome (IT); Anna Taglienti, Rome (IT)

(73) Assignee: Anika Therapeutics S.R.L., Abano Terme (PD) (IT)

( * ) Notice: Subject to any disclaimer, the term of this patent is extended or adjusted under 35 U.S.C. 154(b) by 0 days.

(21) Appl. No.: 13/468,405

(22) Filed: May 10, 2012

(65) Prior Publication Data

US 2013/0184234 A1 Jul. 18, 2013

Related U.S. Application Data

(62) Division of application No. 11/664,754, filed as application No. PCT/EP2005/010645 on Oct. 3, 2005, now Pat. No. 8,563,039.

(30) Foreign Application Priority Data

Oct. 8, 2004 (IT) .............................. PD2004A0245

(51) Int. Cl.
*A61K 9/14* (2006.01)
*A61K 9/00* (2006.01)
*A61K 31/715* (2006.01)
*A61K 47/00* (2006.01)

(52) U.S. Cl.
USPC ........... 424/488; 424/485; 424/400; 514/782; 514/54

(58) Field of Classification Search
CPC ....... A61K 47/36; A61K 8/73; A61K 9/0085; A61K 31/728; A61K 31/715
USPC ..................... 424/488, 485, 400; 514/785, 54
See application file for complete search history.

(56) References Cited

U.S. PATENT DOCUMENTS

| 4,326,053 A | 4/1982 | Kang et al. |
| 5,080,893 A | 1/1992 | Goldberg et al. |
| 6,339,074 B1 | 1/2002 | Cialdi et al. |
| 6,579,978 B1 | 6/2003 | Renier et al. |
| 6,596,704 B1 | 7/2003 | Court et al. |
| 2002/0037874 A1 | 3/2002 | Renier et al. |
| 2003/0181689 A1 | 9/2003 | Bellini et al. |
| 2003/0219431 A1 | 11/2003 | Petti et al. |

FOREIGN PATENT DOCUMENTS

| EP | 0 940 410 | 9/1999 |
| WO | 99/04828 | 2/1999 |

*Primary Examiner* — Abigail Fisher
(74) *Attorney, Agent, or Firm* — Ladas & Parry LLP

(57) ABSTRACT

New biomaterials consisting of a combination of sulphated hyaluronic acid and gellan (as well as gellan that has not been associated with other polymers), to be used as a highly effective barrier to prevent post-surgical adhesions in abdominal, pelvic and, above all, spine surgery.

21 Claims, 1 Drawing Sheet

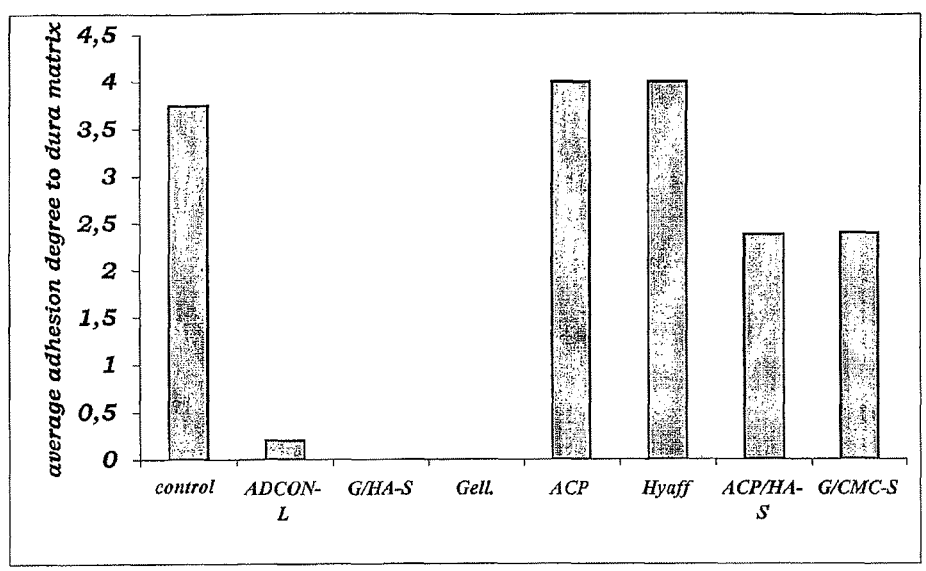

BIOMATERIALS CONSISTING OF SULPHATED HYALURONIC ACID AND GELLAN TO BE USED IN THE PREVENTION OF SPINAL ADHESIONS

RELATED APPLICATION INFORMATION

The present application is a divisional application of U.S. patent application Ser. No. 11/664,754 filed on Aug. 22, 2008 now U.S. Pat. No. 8,563,039, which is a 371 of International Application PCT/EP05/10645 filed on 3 Oct. 2005 and entitled "Biomaterials Consisting Of Sulphated Hyaluronic Acid And Gellan To Be Used In The Prevention Of Spinal Adhesions", which was published in the English language on 13 Apr. 2006, with International Publication Number WO 2006/037592, and which claims priority from Italian Patent Application PD 2004 A 000245, filed 8 Oct. 2004.

SUBJECT OF THE INVENTION

The present invention concerns new biomaterials consisting of a combination of sulphated hyaluronic acid and gellan (as well as gellan that has not been associated with other polymers), for use as a highly effective barrier to prevent post-surgical adhesions in abdominal, pelvic and, above all, spine surgery.

BACKGROUND OF THE INVENTION

The formation of post-surgical adhesions is a very common complication which occurs in up to 70-90% of cases following abdominal or pelvic surgery (Holmdahl L. et al., Eur J Surg 1997, 163(3):169-174), and in up to 40% of cases of spine surgery (Einhaus S L et al., Spine 1997, 22(13):1440-1447).

Many factors determine and/or influence the formation of post-surgical adhesions, such as mechanical trauma, post-operative bleeding, the onset of ischaemic and inflammatory phenomena and possible microbial infections.

The serous exudate that forms as a consequence of surgical trauma, if not rapidly reabsorbed, may determine notable fibroblast recruitment with consequent deposit of collagen molecules responsible for the formation of adhesion between adjacent tissues.

In conclusion, the formation of a post-surgical adhesion seems to be the direct consequence of an inflammatory process.

In the field of spine surgery, the formation of peridural fibrosis is a major post-operative risk. Indeed, following laminectomy and/or discectomy, the fibrous astrocytes (cells characteristic of the glia) produce gliotic scar tissue, the function of which is to prevent neuronal matter from leaking from the dura matrix, the outermost of the meninges covering the spinal cord, formed by fibrous connective tissue.

This is a normal phenomenon in the healing process of damaged spinal tissues, but in the post-surgical inflammatory process, this totally inelastic adhesion tissue may be produced in excess and interfere with the neuromotor processes of the nerve root and dura matrix, crush the adjacent tissues and anatomical structures, thus causing the normal movements of the spinal cord and limbs to be painful.

Any subsequent operations would be more complex, requiring longer hospitalization and less optimistic prognoses.

For the above reasons, the prevention and/or inhibition of post-surgical adhesions, specifically peridural fibrosis, have become major objectives in medical and pharmaceutical scientific research.

Indispensable features of an effective anti-adhesion barrier are: biodegradability and biocompatibility, low or no toxicity, good adhesiveness and handling, no interference with the natural healing process of the damaged tissues, but above all the ability to prevent adhesions that may form between adjacent tissues subjected to abdominal or spine surgery.

Many different materials have been tested (both in vitro and in vivo) as possible new anti-adhesives, such as synthetic or semisynthetic membranes of polyethylene terephthalate (Dacron®, metacrylate, polylactic acid (Klopp L S et al., Neurosurg Focus 2004, 16(3):E2), polytetrafluoroethylene (Goretex® (Llado A et al., Eur Spine 1999, 8(2): 144-150).

Other experiments have investigated the effects of irrigating with steroid and non-steroid drugs, but these materials did not meet all the necessary requirements (described above) for an anti-adhesive that can be used effectively and safely in clinical practice.

U.S. Pat. Nos. 5,017,229, 5,527,893 and 5,760,200 disclose a new type of anti-adhesive membrane (Seprafilm®) consisting of two chemically bound polymers, such as hyaluronic acid (HA) and carboxymethyl-cellulose; however, the efficacy of the new barrier is diminished by toxicity problems linked with the use of activating agents such as carbodiimide, that are necessary to the formation of chemical bonds between the two polymers.

U.S. Pat. No. 5,605,938 describes an anti-adhesive medical device (ADCON®-L) consisting of a resorbable and extrudable gel, composed of pig gelatin and dextran sulphate. The ADCON®-L gel proved very effective in the prevention of post-surgical adhesions and, for this reason, it was used by the Applicant as a control device in the animal experiments described hereafter.

Conversely, EP 1323436 discloses a new anti-adhesion barrier deriving from the combination of carboxymethyl cellulose and gellan, in a 1:(0.2-5) weight ratio. The cellulose derivative in this case represents the active agent in the adhesion prevention process, however it is known to be completely without anti-inflammatory and/or antimicrobial properties, unlike sulphated hyaluronic acid (SHA) (EP0702699 B 1), the active agent in the new anti-adhesion barrier that is the subject of the present invention.

Studies have also been performed on hyaluronic acid that has not been chemically modified (U.S. Pat. No. 4,141,973), to investigate its properties as an anti-adhesion barrier, but as the polymer is easily hydrated and biodegraded, its residence time in situ is far too short to enable the complete prevention of adhesions.

For this reason, hyaluronic acid has been modified to form ester bonds inside the molecule (EP 0341745 B1) which make it effective in preventing both abdominal and pelvic adhesions (Hyalobarrier® gel based on ACP® gel) by markedly increasing the residence time of the polymer at the lesion site (EP 0850074).

The esters of hyaluronic acid (EP 0216453 B1), especially its benzyl ester (Hyaff®-11), have proved efficacious in preventing post-surgical adhesions (U.S. Pat. No. 6,723,709) as well, especially when used to make solid structures such as non-woven felts (EP 0618817 B1).

However, the validity of modified hyaluronic acid in spine surgery has never been tested.

SUMMARY OF THE INVENTION

The present invention relates to a new biomaterial deriving from the combination of sulphated hyaluronic acid and gellan, as well as to a new biomaterial exclusively formed by the gellan polymer. The biomaterials of the invention proved highly effective in preventing post-surgical adhesions, both abdominal and pelvic, and especially effective in the total prevention of the adhesions that form after spine surgery, such as laminectomy and discectomy.

BRIEF DESCRIPTION OF THE DRAWING

The FIGURE illustrates the results obtained from anatomical assessment of tested anti-adhesion devices and controls as described in the Examples.

DETAILED DESCRIPTION OF THE INVENTION

The present invention relates to a new biomaterial consisting of consisting of combination sulphated hyaluronic acid, or other sulphated derivatives of hyaluronic acid, and gellan, as well as a new biomaterial formed by gellan alone, as new medical devices for the complete prevention of post-surgical adhesions, both abdominal and pelvic, and especially adhesions that form after spine surgery.

Indeed, the biomaterials that are the object of the present invention proved effective in completely preventing the adhesions that frequently form after operations for laminectomy/discectomy, or as a consequence of spine surgery of various kinds.

It has been found that sulphated hyaluronic acid plays a fundamental role in preventing adhesions: in fact, the presence of the carboxy groups of the polysaccharide, together with its sulphated groups, determines strong electrostatic repulsion with regard to the fibroblasts, thus inhibiting cell invasion of the damaged spinal tissue. Gellan, on the other hand, acts as a structural matrix able to control the absorption of sulphated hyaluronic acid by the treated tissues, while acting as a support for the biomaterial (preferably in the form of a gel) maintaining its initial consistency for as long as it takes effectively to exercise its role as anti-adhesion barrier.

Sulphated hyaluronic acid, related preparation process and its use as an anti-adhesion device are described and claimed in EP 0702699 B1. However, SHA chemical-physical characteristics are such that a gel constituted solely by said polymer would possess viscosity comparable to that of HA that has not been chemically modified. Indeed, SHA has proved to be more easily hydrated than the non-sulphated polysaccharide and to have the same biodegradability. For these reasons, SHA itself cannot be used as a biomaterial for the prevention of post-surgical adhesion because its residence time in situ is totally insufficient for the complete prevention of adhesions.

The combination of sulphated hyaluronic acid and gellan, on the other hand, has proved to be optimal, since the experiments performed on animals (and subsequently described) have shown that the formation of fibrous tissue around the dura matrix meningeal membrane is negligible compared to that of the untreated controls, both with regard to the untreated controls and to the ADCON®-L device (anti-adhesive long used in clinical practice) and that, consequently, there is no adhesion or compression of the scar tissue to the dura matrix.

EP 0702699 B1 discloses new hyaluronic acid derivatives obtained by a process of sulphation of the polysaccharide that leads to the formation of molecules of sulphated hyaluronic acid (that may sulphated to varying degrees) with specific anticoagulant and antithrombotic properties, for the preparation of new medical devices.

Conversely, the Applicant has demonstrated that the presence of sulphated groups chemically bound to hyaluronic acid in the biomaterial of the invention does not interfere with the normal blood clotting process.

Moreover, the biomaterial of the present invention also has anti-inflammatory and antimicrobial properties, thus proving to possess all the characteristics necessary for an effective anti-adhesive agent.

Gellan is an exopolysaccharide of microbial origin, produced from the Sphingomonas elodea micro-organism by aerobic fermentation. Native gellan is a heteroglycan resulting from the linking of repeating tetrasaccharide units consisting of consisting of glucose, glucuronic acid and rhamnose, in a 2:1:1 molar ratio.

Deacylation of gellan (by basic hydrolysis) gives the commercial product Gelrite®, which is used in the present invention as it is, or in combination with sulphated hyaluronic acid or with its sulphated derivatives.

In its natural state, gellan forms gels that are weak but elastic and flexible, while deacetylated gellan forms compact gels in the same conditions.

Gellan can be used in the fields of foodstuffs, biotechnology and pharmaceuticals. It is used in foods as a thickener and stabiliser and in vegetal biotechnology as a substrate (solid) for growing bacterial cultures. In the pharmaceutical industry, gellan is used in the formation of slow-release microcapsules, owing to its ability to form a gel in the presence of cations.

Hyaluronic acid is a hetero-polysaccharide composed of alternating residues of D-glucuronic acid and N-acetyl-D-glucosamine. It is a straight-chained polymer with a molecular weight that varies between 50,000 and $13 \times 10^6$ Daltons (Da), according to the source from which it was obtained and the methods used to prepare it. It is present in nature in the pericellular gels, in the fundamental substance of the connective tissue of vertebrate organisms (of which it is one of the main components), in the synovial fluid of joints, in the vitreous humor and umbilical cord.

HA plays an important role in the organism, especially as a mechanical support for the cells of many tissues, such as the skin, tendons, muscles and cartilage. Moreover, as it is the main component of the extracellular matrix, it plays and/or takes part in other biological functions, such as tissue hydration, joint lubrication, cell migration and differentiation.

Because of its bio/mucoadhesive properties and tissue compatibility features, hyaluronic acid and the salts thereof (in particular, sodium, potassium, magnesium and calcium salts, possibly suitably derivatised), have been proposed as both systems for the controlled release of drugs and for the preparation of medical devices such as prostheses.

The HA used in the present invention may be derived from any source, for example, it may be extracted from rooster combs (EP 0138572 B1), obtained by fermentation (EP 0716688 B1), or by technological means, and it may have a molecular weight ranging from 400 to $3 \times 10^6$ Da, in particular from 10,000 to $1 \times 10^6$ Da, and more particularly between 100,000 and 250,000 Da.

The process for the sulphation of hyaluronic acid and the derivatives thereof can be performed in a manner known to those skilled in the art, but preferably as disclosed in EP 0702699 B1.

The HA derivatives that can be used in the sulphation process are listed hereafter:
1. HA salified with organic and/or inorganic bases with a molecular weight of 50-730 KDa (EP 0138572 B1) or with a high molecular weight of 750-1230 KDa (EP 535200 B1); preferably with a molecular weight between 100 and 250 KDa;
2. Hyaff®: esters of HA with alcohols of the aliphatic, araliphatic, cycloaliphatic, aromatic, cyclic and heterocyclic series (EP 216453 B1); the percentage of esterification of the hyaluronic acid that subsequently undergoes sulphation may vary between 5 and 65%, according to the type and length of the alcohol used as the resulting product must be water-soluble;

3. ACP®: inner esters of HA (EP 0341745 B1); the percentage of inner esterification of hyaluronic acid that subsequently undergoes sulphation may vary between 1 and 15% as the resulting product must be water-soluble;

4. Hyoxx™: percarboxylated HA derivatives obtained by oxidation of the primary hydroxyl of the N-acetyl-glycosamine fraction, (EP 1339753); the percarboxylation percentage of the hyaluronic acid that subsequently undergoes sulphation may vary between 1 and 50%.

All the free carboxy groups of HA may be salified with organic and/or inorganic bases.

The sulphation degree of hyaluronic acid and/or the derivatives thereof listed above, in terms of number of sulphated groups per repeating unit, may vary between 0.5 and 3.5 and should preferably be 3.

A number of pharmacologically and/or biologically active substances may possibly be associated with the main components of the biomaterial of the present invention, to increase its anti-adhesion efficacy. In particular, antibiotics and drugs classified as protein inhibitors such as Interleukin (IL)-10, IL-13, IL-1, TNF and Interferone.

The anti-adhesion devices of the invention can be made in various forms: sponges, gels or hydrogels, foams or powders, the preferred form being a gel or hydrogel.

The weight ratio between gellan (G) and SHA (or between G and the sulphated derivatives of HA), may vary between 1.5:1, 2:1 and lastly 2:1.5; a 2:1 weight ratio being preferred. Alternatively, as previously described, the gellan may be used as such, preferably in the form of a gel or hydrogel, as a new, spinal, anti-adhesion biomaterial.

In the following, some examples of the preparation of the anti-adhesion biomaterials of the present invention, together with the results from in vivo experiments, are reported.

Example 1

Preparation of the Biomaterial in the Form of a Hydrogel Consisting of Gellan in Combination with Sulphated Ha in 2:1 Weight Ratio The HA is sulphated according to EP 0702699 B1 with a degree of sulphation of 3.

A solution of 20 mg/ml of deacetylated gellan (Gelrite® is prepared by heating (75-85° C.) and dissolving 1 g. of gellan in 50 ml of NaCl, 0.9%. Once solubilisation is complete, 500 mg of sulphated HA is added and left to dissolve completely. The mixture is then cooled to room temperature until a hydrogel is obtained which can then be steam-sterilised.

Example 2

Preparation of the Biomaterial in the Form of a Hydrogel Consisting of Gellan in Combination with Sulphated HA, 1.5:1 Weight Ratio Proceed as for Example 1, dissolving 750 mg of gellan and 500 mg of sulphated HA.

Example 3

Preparation of the Biomaterial in the Form of a Hydrogel Consisting of Gellan in Combination with Sulphated HA Benzyl Ester, with 25% Esterification, 2:1 Weight Ratio The gellan solution is prepared as described in Example 1. 500 mg of sulphated HA benzyl ester is then added and left till solubilisation is complete. It is then left to cool to room temperature giving a hydrogel that can then be steam-sterilised.

Example 4

Preparation of the Biomaterial in the Form of a Powder Consisting of Gellan in Combination with Sulphated HA, 2:1 Weight Ratio Proceed as for Example 1 but, after solubilisation of the sulphated HA, the still-warm solution is slowly poured into absolute ethanol cooled to 4° C. The resulting precipitate is then separated from the solvent by filtering. The resulting powder is dried with the aid of a high-vacuum system.

Example 5

Preparation of the Biomaterial in the Form of a Sponge Consisting of Gellan in Combination with Sulphated HA, 2:1 Weight Ratio Proceed as for Example 1. The final solution obtained after cooling to room temperature is then subjected to a lyophilisation cycle. A three-dimensional structure in the form of a sponge is thus obtained.

Example 6

Preparation of a Biomaterial in the Form of a Hydrogel Exclusively Constituted by Gellan A 20 mg/ml solution of deacetylated gellan is prepared (the concentration may vary between 1 and 50 mg/ml) by dissolving, after heating (75-85[deg.] C.), 1 g. of gellan, Kelcogel® CG-LA (viscosity 32 Cp), in 50 ml of 0.9% NaCl. Complete solubilisation usually takes between 3 and 5 minutes. (The time it takes for the gellan powder to dissolve depends on its viscosity, which may vary between 26 and 39 Cp). The solution is left to cool at room temperature until a hydrogel is obtained which can be steam-sterilised.

Preclinical Experiments

Experiments were performed on laboratory animals to demonstrate the complete efficacy and safety of the new biomaterial of the present invention.

Anti-Adhesion Devices Tested

The biomaterials that were tested on laboratory animals were:

ADCON®-L, a medical device in gel form, composed of pig gelatin and sulphated dextran, an anti-adhesive of proven clinical efficacy used as control;

ACP® gel, consisting of inner esters of HA with 5% inner esterification, prepared in saline at a concentration of 60 mg/ml;

Hyaff®-11 gel: benzyl ester of HA esterified to a degree of 50%; prepared in saline at a concentration of 70 mg/ml;

G/SHA gel: formed by the combination of G and SHA, prepared in saline in a Gellan to sulphated HA 2:1 weight ratio (see Example 1);

G/CMC-S gel: consisting of the combination of Gellan and Carboxymethylcellulose sulphate (CMC-S) prepared in saline in a 1.5:1 weight ratio;

ACP®/SHA gel: formed by ACP® and SHA, prepared in saline as an association between the polymers in a 5:1 weight ratio;

Gellan gel prepared according to Example 6

Experimental Model of Formation of Post-Surgical Adhesions Following Spine Surgery 24 New Zealand rabbits weighing on average 2.5 kg were used. Each animal was anaesthetized by administering intravenously a solution of Zoletil/Rompun/saline (1:0.5:3.5 v/v/v, 0.25 ml/kg); all the animals were operated on at a lumbosacral level at two separate vertebral sites: L2 and L4.

After performing an incision of 5 cm along the spinous processes of the corresponding area, the underlying muscle fascia was then incised and any excessive bleeding was staunched by cauterisation. Subsequently, laminectomy was performed (5×10 mm in size) at a level of the lumbar vertebrae L2 and L4, thus exposing the dura matrix and the nerve roots that emerge from the corresponding area of the spinal cord.

At this point of the operation, the previously listed anti-adhesion devices were applied and the muscle fascia and overlying skin were stitched back in place.

Three animals served as negative controls. They were operated on in the same way but did not receive any anti-adhesion treatment to assess the level of adhesion and compression of the fibrous tissue that forms with regard to the dura matrix.

A total of 24 animals were operated on at 2 different sites and 7 devices were analysed. Taking into account the negative controls, each device was tested on 3 animals for a total of 6 spinal sites per device.

Analyses
Prothrombin Time (PT)

One month after surgery, all the animals were sacrificed. Blood samples were taken from the 3 negative control animals and the 3 animals treated with G/SHA gel 3 days before surgery and on the 21st day of treatment for specific haemodynamic tests (PT) to assess any effects of SHA on blood coagulation, by comparing the blood from the treated animals with that of the untreated controls (Mennmeyer S T et al., JAMA 1993, 269(8):1030-1033).

Histological Analysis

Samples were taken from the spinous processes (zones L2 or L4) of the animals treated with G/SHA and those treated with ADCON®-L, as well as from the animals belonging to the negative control group. The samples were then prepared for histological analysis: the samples were fixed in 10% formalin then immersed in a decalcifying solution consisting of formalin/nitric acid/distilled water (Oct. 5, 1985). Samples were then dehydrated in alcohol, embedded in paraffin, then sliced into sections 5 μm thick and stained with haematoxylin and eosin.

Subsequent analysis revealed the formation of fibrous tissue and its adhesion to the dura matrix, expressed in terms of a score after analysis of all the samples, as follows:

Grade 0=no fibrous tissue present near the dura matrix;
Grade 1=a thin fibrous tissue is visible between the newly-formed scar tissue and the dura matrix;
Grade 2=presence of fibrous tissue adhering to the dura matrix affecting almost ⅔ of the area treated by laminectomy;
Grade 3=presence of fibrous tissue that causes compression and adheres completely to the dura matrix, affecting over ⅔ of the area treated by laminectomy.

Anatomical Observations

After sacrifice, all the animals were examined at the site of laminectomy. The dura matrix and nerve roots were then exposed again to assess the presence of adhesions and compression in terms of the following scoring system:

Grade 0=no fibrous tissue visible near the dura matrix;
Grade 1=a thin layer of fibrous tissue can be seen adhering to the dura matrix;
Grade 2=presence of fibrous tissue moderately adhering to the dura matrix;
Grade 3=presence of fibrous tissue compressing and adhering markedly to the dura matrix.
Grade 4=presence of fibrous tissue in a sufficient quantity to occupy the entire space affected by surgery.

Results Obtained
Assessment of Prothrombin Time (PT):

Table 1 shows the PT values of the blood samples taken from the animals treated with G/SHA versus the untreated controls

| untreated samples: PT measured 3 days before surgery | untreated samples: PT measured 28 days after surgery | treated samples: PT measured 3 days before surgery | treated samples: PT measured 28 days after surgery |
|---|---|---|---|
| PT = 7.5 sec. | PT = 7.6 sec. | PT = 7.6 sec | PT = 7.8 sec. |

The results show that there was no change in PT before and after surgery either in the controls or in the treated animals, thus indicating that SHA in combination with gellan, used as an anti-adhesion biomaterial, did not in any way affect the blood coagulation time in the treated animals.

Histological Assessment:

Table 2 shows the scores given to the treated samples, as described above, versus the untreated samples which acted as negative controls.

| Samples | Mean score graded according to the formation of fibrous tissues | Mean score graded according to the formation of adhesion to the dura matrix |
|---|---|---|
| Control | Grade 1.5 | Grade 2 |
| G/SHA | Grade 0.3 | Grade 0 |
| ADCON®-L | Grade 1.1 | Grade 1.8 |

The results show unequivocally that the biomaterial of the present invention is totally effective in preventing the formation of fibrous tissue adhering to and compressing the dura matrix meningeal membrane and, consequently also the nerve roots that protrude from the spinal cord.

Anatomical Observation:

FIGURE illustrates the results obtained from anatomical assessment, expressed as scores from 0 to 4, of all the anti-adhesion devices tested, versus the related untreated controls.

As can clearly be seen from the FIGURE, G/SHA and gellan as such, the new anti-adhesion agents of the present invention completely prevent the formation of post-surgical spinal adhesions, giving far better results than the ADCON®-L device, which is normally used in clinical practice in view of its proven efficacy.

Lastly, the above graph shows that SHA is neither equivalent to nor can be substituted by any other semisynthetic sulphated polymer such as CMC-S. Indeed, its combination with gellan (G/CMC-S) gives a decidedly negative result, especially when compared to that obtained with G/SHA gel.

The invention being thus described, it is clear that the examples of preparation of the biomaterial that is the subject of the invention can be modified in various ways. Such modifications are not to be considered as divergences from the spirit and purpose of the invention, and any such modification that would appear evident to an expert in the field comes within the scope of the following claims.

The invention claimed is:

1. A method for the prevention or mitigation of post-surgical adhesions comprising application of biomaterials wherein the active ingredients consist of the combination of deacylated gellan and sulphated hyaluronic acid to sites susceptible to such adhesions.

2. The method according to claim 1 for the prevention or mitigation of post-surgical spinal adhesions.

3. The method according to claim 2 in which the sulphated hyaluronic acid has a degree of sulphation between 0.5 and 3.5.

4. The method according to claim 3 in which the sulphated hyaluronic acid has a degree of sulphation equal to 3.

5. The method according to claim 2 in which the sulphated hyaluronic acid has a molecular weight ranging from 10,000 to $1 \times 10^6$ Da.

6. The method according to claim 2 in which the weight ratio between gellan and sulphated hyaluronic acid is between 1.5:1, and 2:1.

7. The method according to claim 2 in which the weight ratio between gellan and sulphated hyaluronic acid is between 2:1 and 2:15.

8. A method for prevention or mitigation of post-surgical adhesions comprising application of biomaterials wherein the active materials consist of the combination of deacylated gellan and sulphated hyaluronic acid derivatives to sites susceptible to such adhesions.

9. The method according to claim 8 for prevention or mitigation of post-surgical spinal adhesions.

10. The method according to claim 9 in which the sulphated hyaluronic acid derivatives have a degree of sulphation of between 0.5 and 3.5.

11. The method according to claim 10 in which the sulphated hyaluronic acid derivatives have a degree of sulphation equal to 3.

12. The method according to claim 9 in which the sulphated hyaluronic acid derivatives have a molecular weight ranging from 10,000 to $\times 10^6$ Da.

13. The method of the biomaterials according to claim 9 in which the weight ratio between gellan and the sulphated hyaluronic acid derivatives is between 1.5:1 and 2:1.

14. The method according to claim 9 in which the weight ratio between gellan and sulphated hyaluronic acid is between 2:1 and 2:1.5.

15. The method according to claim 9 in which the hyaluronic acid derivatives which may be sulphated are constituted by:
   i Hyaff®: esters of hyaluronic acid with a percentage of esterification of between 5 and 65%;
   ii ACP®: inner esters of hyaluronic acid with a percentage of inner esterification of between 1 and 15%;
   iii Hyoxx™: percarboxy derivatives of hyaluronic acid with a percentage of percarboxylation of between 1 and 50%.

16. The method according to claim 5, in which the sulphated hyaluronic acid has a molecular weight of from 100,000 to 250,000 Da.

17. The method according to claim 6, in which the weight ratio between gellan and sulphated hyaluronic acid is 2:1.

18. The method according to claim 12, in which the sulphated hyaluronic acid derivatives have a molecular weight of from 100,000 to 250,000 Da.

19. The method of the biomaterials according to claim 13 in which the weight ratio between gellan and the sulphated hyaluronic acid derivatives is equal to 2:1.

20. A method for the prevention or mitigation of post-surgical adhesions comprising application of biomaterials wherein the active ingredients consist of the combination of deacylated gellan and sulphated hyaluronic acid to sites susceptible to such adhesions wherein said biomaterials are made in the form of sponges, gels or hydrogels, foams or powders.

21. A method for the prevention or mitigation of post-surgical adhesions comprising application of biomaterials wherein the active ingredients consist of the combination of deacylated gellan and sulphated hyaluronic acid derivatives to sites susceptible to such adhesions wherein said biomaterials are made in the form of sponges, gels or hydrogels, foams or powders.

* * * * *